United States Patent
Nakano et al.

(12) 
(10) Patent No.: US 6,463,788 B2
(45) Date of Patent: Oct. 15, 2002

(54) STRUCTURE OF ELECTRIC CONNECTOR OF GAS SENSOR

(75) Inventors: Norihiko Nakano, Anjo (JP); Hirokazu Yamada, Aichi-ken (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/860,781

(22) Filed: May 21, 2001

(65) Prior Publication Data

US 2002/0017127 A1 Feb. 14, 2002

(30) Foreign Application Priority Data

May 22, 2000 (JP) ........................................ 2000-150330
Feb. 26, 2001 (JP) ........................................ 2001-051039

(51) Int. Cl.[7] ........................ G01N 27/04; G01N 30/02; G01N 27/409; G01M 15/00; H01C 7/00
(52) U.S. Cl. ..................... 73/31.05; 73/23.31; 204/424; 422/94
(58) Field of Search ............................. 73/31.05, 23.31, 73/23.32; 324/450; 422/90, 94; 204/424, 428

(56) References Cited

U.S. PATENT DOCUMENTS

| | | | |
|---|---|---|---|
| 4,214,472 A | * 7/1980 | Maxwell et al. | 73/23.31 |
| 4,309,897 A | * 1/1982 | Springer et al. | 73/23.31 |
| 4,443,781 A | * 4/1984 | Ohta et al. | 338/34 |
| 4,535,316 A | * 8/1985 | Wertheimer et al. | 338/34 |
| 5,490,412 A | * 2/1996 | Duce et al. | 73/23.31 |
| 5,616,825 A | * 4/1997 | Achey et al. | 73/23.31 |
| 5,739,414 A | * 4/1998 | Paulus et al. | 73/23.31 |
| 5,874,663 A | * 2/1999 | Fukaya et al. | 73/23.32 |
| 5,874,664 A | * 2/1999 | Watanabe et al. | 73/23.32 |
| 5,886,248 A | * 3/1999 | Paulus et al. | 73/23.31 |
| 5,955,656 A | * 9/1999 | Graser et al. | 73/23.31 |
| 6,347,543 B1 | * 2/2002 | Geier et al. | 73/23.31 |

FOREIGN PATENT DOCUMENTS

| | | |
|---|---|---|
| EP | 0506897 | 12/1995 |
| JP | 4-110972 | 9/1992 |

* cited by examiner

*Primary Examiner*—Daniel S. Larkin
*Assistant Examiner*—David J. Wiggins
(74) *Attorney, Agent, or Firm*—Nixon & Vanderhye P.C.

(57) ABSTRACT

An improved structure of an electric connector of a gas sensor is provided which is designed to establish a firm electric connection between each electrode terminal formed on a sensing element and one of plural leads extending outside of the gas sensor for connection with an external device. The connector has a stopper which is placed in contact with an end wall of an insulating member to keep the connector on the insulating member without the connector dropping into a hole through which a lead extends from the sensing element when the lead is coupled to the connector. This allows the connector to be pressed and welded to secure the lead in a constant position relative to the insulating member, thus improving the stability of the sensor signal to be received at the external device.

16 Claims, 13 Drawing Sheets

STRUCTURE OF ELECTRIC CONNECTOR OF GAS SENSOR

BACKGROUND OF THE INVENTION

1. Technical Field of the Invention

The present invention relates generally to a gas sensor which may be installed in an exhaust system of an internal combustion engine for air-fuel ratio control, and more particularly to an improved structure of an electric connector used in such a gas sensor.

2. Background Art

EP0506897 discloses a typical laminated gas sensor. This sensor has the disadvantage that a structure for providing a sensor signal to an external device is complex and results in instability of the sensor signal. The present invention is directed to an improved structure of a gas sensor which is capable of outputting a sensor signal accurately.

SUMMARY OF THE INVENTION

An oxygen concentration measuring gas sensor, as will be described below in detail, may be proposed as being installed in an exhaust system of an internal combustion engine for air-fuel ratio control.

The gas sensor includes a sensor element, a sensor element side insulation porcelain, an atmospheric side insulation porcelain, a hollow cylindrical housing, and an atmospheric cover. The sensor element side insulation porcelain is made of a cylindrical member and retains therein the sensor element. The atmospheric side insulation porcelain is disposed in alignment with the sensor element side insulation porcelain to cover a base portion of the sensor element. The housing retains therein the sensor element side insulation porcelain. The atmospheric cover is disposed on a base end of the housing to surround the atmospheric side insulation porcelain.

The atmospheric side insulation porcelain has disposed therein a plurality of leads 16, as shown in FIG. 17, connected electrically with the sensor element. Each lead 16 is coupled through a hollow connector 92 electrically to a lead 17 extending outside of the gas sensor.

Each lead 16 is, as clearly shown in FIG. 16(b), inserted into one of the connectors 92 from an end 920, while each lead 17 is, as shown in FIG. 17, inserted into the connector 92 from the other end in alignment with the lead 16. Each of the connectors 92 is, as clearly shown in FIG. 16(a), made of a flat plate bent to a rectangular shape in cross section which is smaller than holes 322 formed in the atmospheric side insulation porcelain 32.

The above structure, however, encounters the drawback in that the connectors 92 may, as shown in FIG. 17, drop partly into the holes 322, which leads to a difficulty in pressing and welding desired portions of the connectors 92 to join them to the leads 16. This problem may be avoided by decreasing the diameter of the holes 322, but it will result in a difficulty in passing the leads 16 through the holes 322. The holes 322 also work as a reference gas induction passage for supplying a reference gas (i.e., air) into a reference gas chamber. The decrease in diameter of the holes 322, thus, also results in a decrease in amount of the reference gas admitted into the reference gas chamber.

It is therefore an object of the invention to provide an improved structure of an electric connector of a gas sensor which is designed to ensure the reliability of electric connection between a sensing element and an external device.

According to one aspect of the invention, there is provided a gas sensor which comprises: (a) a hollow cylindrical housing; (b) a sensing element having a length which includes a sensing portion and a base portion, the sensing element being retained in the housing with the base portion projecting from the housing; (c) a hollow insulating member provided so as to surround the base portion of the sensing element, the insulating member having a wall in which holes are formed; (d) a cover covering the insulating member; (e) first leads each having a first end portion and a second end portion, each of the first end portions being in electric contact with the sensing element within the insulating member, each of the second end portions passing through one of the through holes and projecting outside the insulating member; (f) second leads each having a first end portion and a second end portion, the first end portion extending outside of the gas sensor for electric connection with an external device; and (g) connectors establishing electric connections between the first leads and the second leads, respectively, each of the connectors having a lead joint portion and a stopper, each of the lead-joint portions electrically joining the second end portion of one of the first leads and the second end portion of a corresponding one of the second leads, each of the stoppers being placed in contact with the wall of the insulating member.

In the preferred mode of the invention, each of the stoppers is provided by an extension formed on an end of one of the connectors.

Each of the stoppers may be provided by a portion of one of the connectors which extends outward.

Each of the stoppers may have a tapered end wall for ease of insertion of the second end portion of one of the first leads.

Each of the stoppers may have walls which define a rectangular shape in cross section and have ends expanding outward so that the ends are placed outside one of the holes of the insulating member in contact with the wall of the insulating member.

Each of the connectors may have a longitudinal slit formed therein.

The first leads and the second leads are joined to the connectors by pressing the lead-joint portions of the connector to plastically deform them or welding or soldering the lead-joint portions of the connectors and the first and second leads together.

According to the second aspect of the invention, there is provided a gas sensor which comprises: (a) a hollow cylindrical housing; (b) a sensing element having a length which includes a sensing portion and a base portion, the sensing element being retained in the housing with the base portion projecting from the housing; (c) a hollow insulating member provided so as to surround the base portion of the sensing element, the insulating member having a wall in which holes are formed; (d) a cover covering the insulating member; (e) first leads each having a first end portion and a second end portion, each of the first end portions being in electric contact with the sensing element within the insulating member, each of the second end portions passing through one of the through holes and projecting outside the insulating member; (f) second leads each having a first end portion and a second end portion, the first end portion extending outside of the gas sensor for electric connection with an external device; (g) connectors establishing electric connections between the second end portions of the first leads and the second end portions of the second leads, respectively; and (h) stoppers provided on one of the second end portions of the first leads in contact with the wall of the insulating member.

In the preferred mode of the invention, each of the connectors may have a longitudinal slit formed therein.

The first leads and the second leads are joined to the connectors by pressing the lead-joint portions of the connector to plastically deform them or welding or soldering the lead-joint portions of the connectors and the first and second leads together.

According to the third aspect of the invention, there is provided a gas sensor which comprises: (a) a hollow cylindrical housing; (b) a sensing element having a length which includes a sensing portion and a base portion, the sensing element being retained in the housing with the base portion projecting from the housing; (c) a hollow insulating member provided so as to surround the base portion of the sensing element, the insulating member having a wall in which holes are formed; (d) a cover covering the insulating member; (e) first leads each having a first end portion and a second end portion, each of the first end portions being in electric contact with the sensing element within the insulating member, each of the second end portions passing through one of the through holes and projecting outside the insulating member; (f) second leads each having a first end portion and a second end portion, the first end portion extending outside of the gas sensor for electric connection with an external device; (g) connectors establishing electric connections between the second end portions of the first leads and the second end portions of the second leads, respectively; and (h) stoppers provided in contact with the wall of the insulating member to hold the connectors above the holes of the insulating member.

In the preferred mode of the invention, each of the connectors has a longitudinal slit formed therein.

The first leads and the second leads are joined to the connectors by pressing the lead-joint portions of the connector to plastically deform them or welding or soldering the lead-joint portions of the connectors and the first and second leads together.

According to the fourth aspect of the invention, there is provided a gas sensor which comprises: (a) a hollow cylindrical housing; (b) a sensing element having a length which includes a sensing portion and a base portion, the sensing element being retained in the housing with the base portion projecting from the housing; (c) a hollow insulating member provided so as to surround the base portion of the sensing element, the insulating member having a wall in which holes are formed; (d) a cover covering the insulating member; (e) first leads each having a first end portion and a second end portion, each of the first end portions having a shoulder and being in electric contact with the sensing element within the insulating member, each of the second end portions passing through one of the through holes and projecting outside the insulating member; (f) second leads each having a first end portion and a second end portion, the first end portion extending outside of the gas sensor for electric connection with an external device; (g) connectors establishing electric connections between the second end portions of the first leads and the second end portions of the second leads, respectively; and (h) stoppers each provided by an extension formed on an end of one of the connectors, placed in contact with the shoulder of the first end portion of one of the first leads to hold the one of the connector.

In the preferred mode of the invention, each of the connectors has a longitudinal slit formed therein.

The first leads and the second leads are joined to the connectors by pressing the lead-joint portions of the connector to plastically deform them or welding or soldering the lead-joint portions of the connectors and the first and second leads together.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
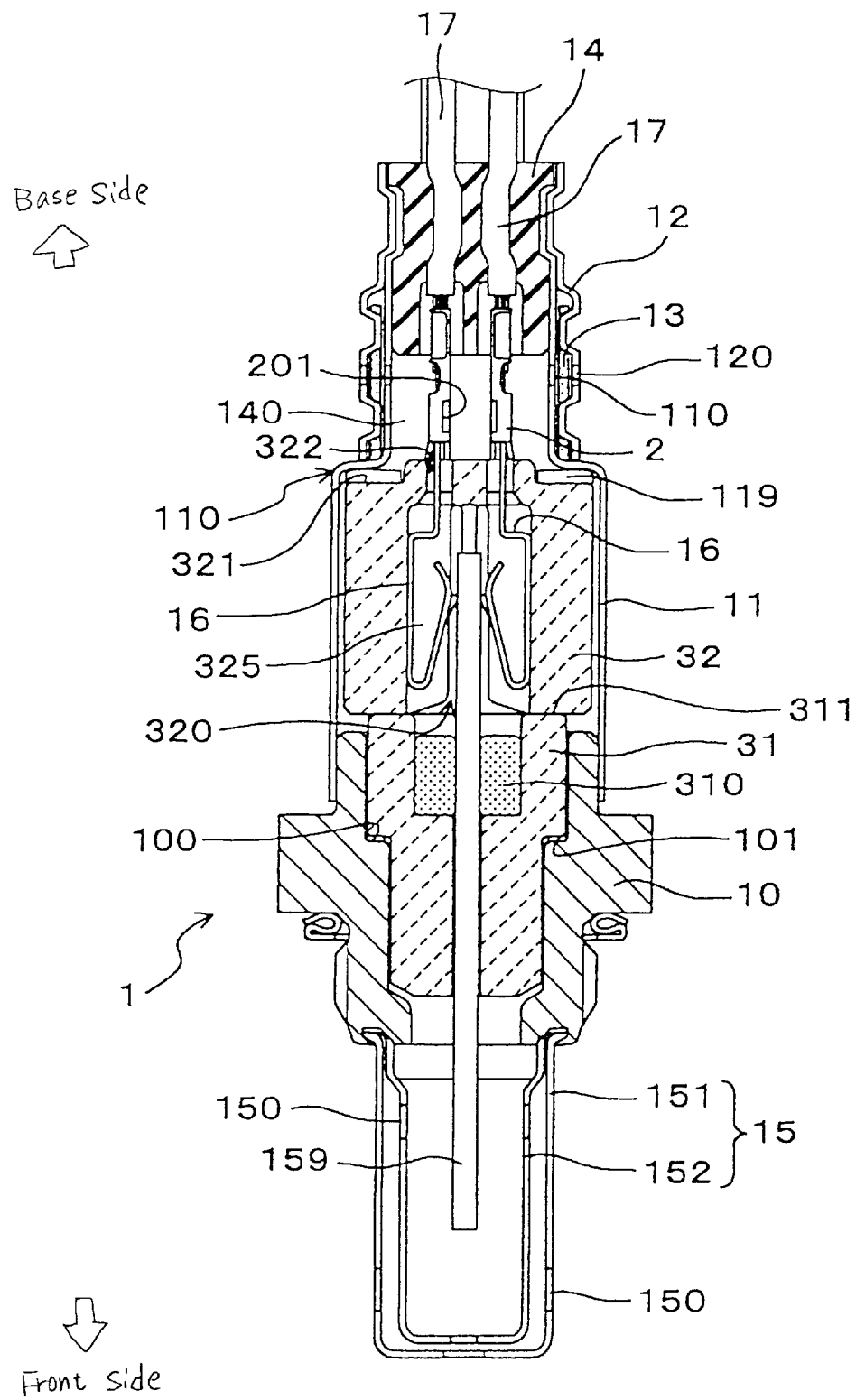
FIG. 1 is a longitudinal sectional view which shows a gas sensor according to the first embodiment of the invention.
Figure 2:
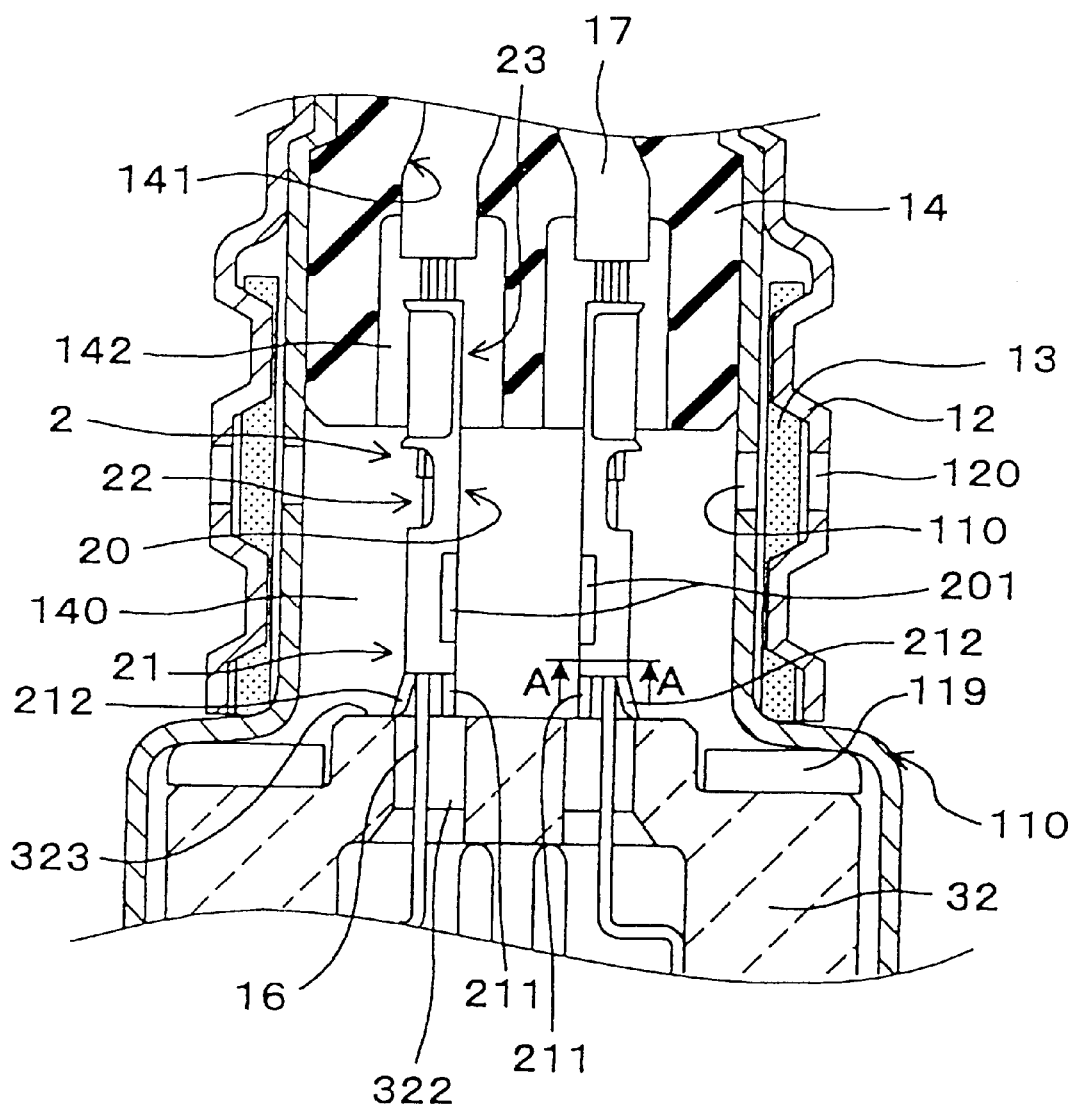
FIG. 2 is a partially sectional view which shows electric connections between a sensing element and leads extending outside a gas sensor.

Referring to the drawings, wherein like reference numbers refer to like parts in several views, particularly to FIGS. 1 and 2, there is shown a gas sensor 1 according to the first embodiment of the invention which may be employed in a burning control system for automotive vehicles to measure concentrations of components such as NOx, CO, HC, and $O_2$ contained in exhaust gasses of the engine.

The gas sensor 1 generally includes a sensor element 159, a first insulation porcelain 31, a second insulation porcelain 32, a hollow cylindrical housing 10, and an air cover 11. The sensor element 159 is made of a laminated plate. For example, U.S. Pat. No. 5,573,650, issued on Nov. 12, 1996 to Fukaya et al. teaches a typical laminated sensor element, disclosure of which is incorporated herein by reference. The first insulation porcelain 31 is fitted within the housing 10 and holds therein the sensor element 159. The second insulation porcelain 32 is mounted on the first insulation porcelain 31 in alignment with each other and surrounds a base portion of the sensor element 159. The air cover 11 is installed at an end thereof on the housing 10 to cover the second insulation porcelain 32.

The second insulation porcelain 32 is made of a hollow cylindrical insulating member and has disposed therein four leads 16 (only two are shown for the simplicity of illustration) each of which is made of a wire folded elastically to make an electric contact at one end with an electrode terminal (not shown) formed on the sensor element 159. The leads 16 extend at the other end through holes 322 formed in an end of the second insulation porcelain 32 and connect with four leads 17 through connectors 2, respectively, for transmission of sensor signals between the sensor element 159 and an external device and supply of electric power to a heater installed on the sensor element 159.

Each of the connectors 2 retains therein the end of one of the leads 6 projecting from the upper end of the second insulation porcelain 32, as viewed in FIG. 1, and the end of one of the leads 17 in alignment with each other to make an electric connection therebetween. Specifically, each of the connectors 2, as will be described later in detail, includes a lead-clamping portion for clamping one of the leads 16 and a connector-holding portion placed in contact with the upper end of the second insulation porcelain 32 to hold the connector 2 on the second insulation porcelain 32. The lead-clamping portion includes a press portion 201. The connector-holding portion is provided by a stopper 212.

Each of the connectors 2 includes a hollow body 20 having the press portion 201 and a head portion 21 having an extension which expands outward to define the stopper 212.

Referring back to FIG. 1, the gas sensor 1 also includes a protective cover assembly 15 consisting of an outer cover 151 and an inner cover 152. The protective cover assembly 15 is installed on a head of the housing 10 to define a gas chamber into which a gas to be measured is admitted through gas holes 150 formed in the outer and inner covers 151 and 152.

The air cover 11 is, as described above, mounted on the base end of the housing 10. An outer cover 12 is provided around the air cover 11 and staked or crimped to retain a water-repellent filter 13 on the periphery of the air cover 11.

The first insulation porcelain 31 is retained within the housing 10 hermetically through a metallic packing ring 101 placed on an annular shoulder 100 formed on an inner wall of the housing 10 and holds therein the sensor element 159 through a glass sealing member 310.

The second insulation porcelain 32 is, as described above, mounted directly on the base end 311 of the first insulation porcelain 31 and surrounded by the air cover 11. The air cover 11 has an upper small-diameter portion, as viewed in the drawing, to form a shoulder 110. A disc spring 119 is disposed between the shoulder 110 and an end of the second insulation porcelain 32 to elastically urge the second insulation porcelain 32 into constant engagement with the first insulation porcelain 31.

The second insulation porcelain 32 has formed therein a chamber 320 which communicates with the four through holes 322 formed in the base end thereof. The chamber 320 opens at the front end of the second insulation porcelain 32 and thus establishes communication between the holes 322 and the outside of the front end of the second insulation porcelain 32.

In the chamber 320, four ribs 325 are provided which work to fix locations of the leads 16 and insulate the leads 16 from each other.

The sensor element 159, as described above, has a heater built therein which heats the sensor element 159 up to a temperature required for the sensor element 159 to be sensitive to a gas to be measured correctly. The sensor element 159 has formed thereon four electrode terminals two of which are used for outputting sensor signals and the others for supply of electric power to the heater. The electrode terminals are connected electrically with ends of the leads 16 in an illustrated manner, respectively. The leads 16 extend through the holes 322 and are inserted into the connectors 2, respectively.

An insulating holder 14 made of rubber is, as clearly shown in FIG. 2, disposed inside the small-diameter portion of the air cover 11. An air chamber 140 is defined between the bottom of the insulating holder 14 and the base end of the second insulation porcelain 32. The insulating holder 14 has formed therein four through holes 141 into which the leads 17 are inserted. The holes 141 have defined therein large-diameter bores 142 in which the leads 17 are joined to the connectors 2, respectively.

Figure 3A:
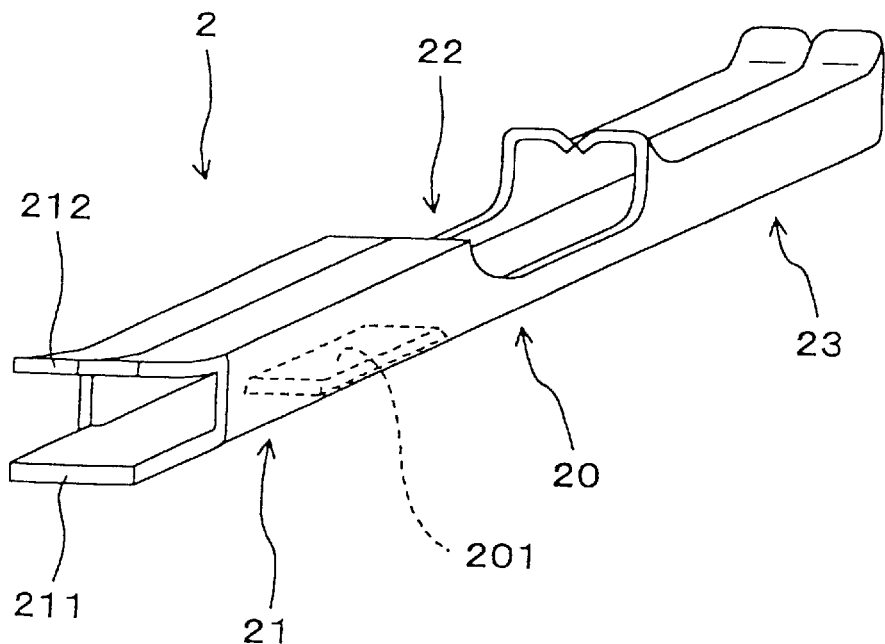
FIG. 3(a) is a perspective view which shows the structure of a connector.

Each of the connectors 2 is, as can be seen from FIG. 3(*a*), made by folding a metallic plate longitudinally into side-to-side contact so as to have a rectangular shape in cross section and consists of the body 20, the head portion 21, and the base portion 23. The lead 17 is retained firmly in the base portion 21. The lead 16 is clamped tightly by the press portion 201 and an opposite inner wall of the body 20.

The body 20 of the connector 2 has a window 22 formed between the press portion 201 and the base portion 23. The press portion 201 is, as clearly shown in FIG. 3(*b*), defined by a dimple which may be formed by a press. The distance r between the press portion 201 and the opposite inner wall of the connector 2 is, thus, shorter than the distance R between opposed inner walls of the head portion 21. In this embodiment, r=0.4 mm, and R=0.6 mm.

The head portion 21 has the stopper 212 and an extension 211. When the lead 16 and the connector 2 are joined together in an assembling process of the gas sensor 1, at least the stopper 212 is placed, as clearly shown in FIG. 2, in contact of an end thereof with an end wall 323 of the second insulation porcelain 32 to hold the connector 2 on the end wall 323 of the second insulation porcelain 32.

How to join each of the leads 17 and 16 to one of the connectors 2 will be described below in detail.

First, the lead 17 (i.e., a bundle of wires from which insulation is removed) is inserted into the base portion 23 of the connector 2 until it reaches a given position. The base portion 23 is clamped or pressed to hold the lead 17 firmly.

Figure 4A:
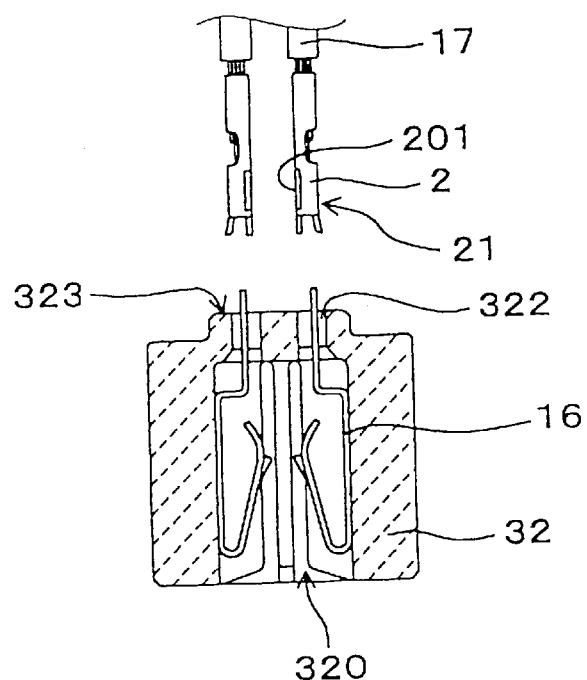
FIGS. 4(a) and 4(b) are views which show a sequence of steps of joining leads to connectors.

Next, the lead 16 is inserted into the second insulation porcelain 32 from the front end thereof (i.e., the lower end as viewed in FIG. 1) and drawn, as shown in FIG. 4(a), at an end thereof out of the hole 322.

Figure 3B:
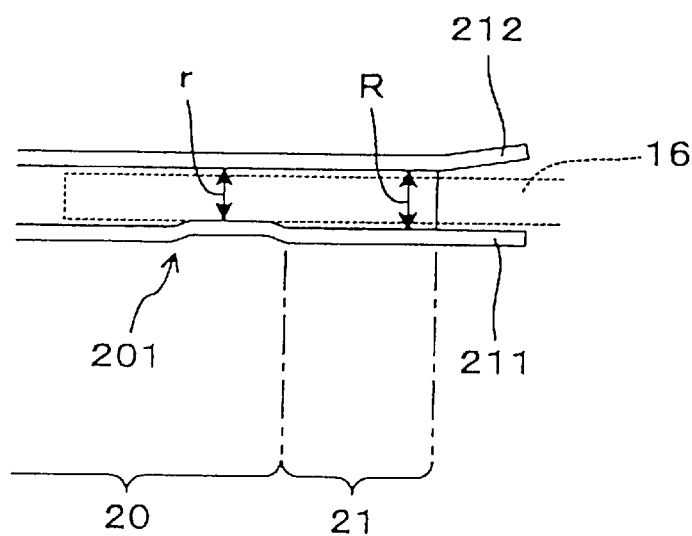
FIG. 3(b) is a longitudinal sectional view which shows the connector of FIG. 3(a)
Figure 4B:
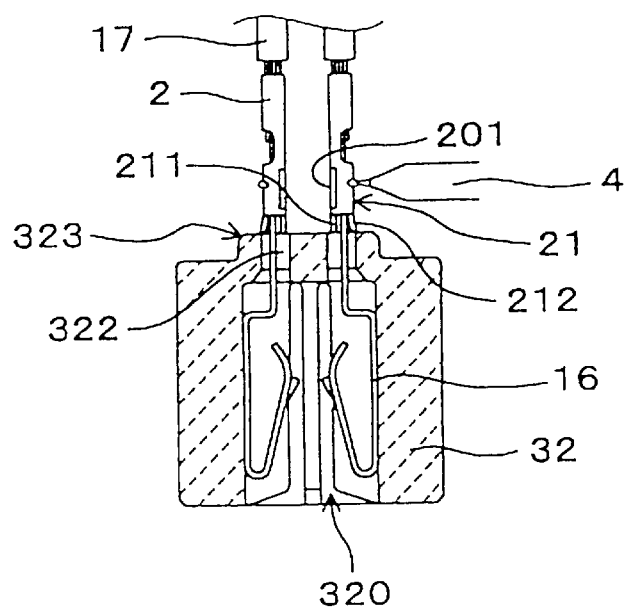

The connector 2 to which the lead 17 is joined is put on the end of the lead 16 projecting from the hole 322 of the second insulation porcelain 32 in contact of the stopper 212 and the extension 211 with the end wall 323 of the second insulation porcelain 21, so that the end of the lead 16 is, as shown in FIG. 3(b), inserted into the connector 2 over the press portion 201. The pressure is applied to the press portion 201 to deform it to hold the end of the lead 16 firmly in the connector 2. Subsequently, a laser beam is, as shown in FIG. 4(b), radiated to a given portion of the peripheral wall of the connector 2 using a laser welding device 4 to weld the connector 2 to the lead 16. The connector 2 and the lead 16 may alternatively be soldered together.

Finally, the base of the sensor element 159 fitted in the first insulation porcelain 31 is inserted into the center of the chamber 320 of the second insulation porcelain 32 to make electric connections between the electrode terminals formed on the sensor element 159 and the leads 16.

As apparent from the above discussion, the stopper 212 extends outward from the head portion 21 of the connector 2 so that the end of the connector 2 may be kept in contact with the end wall 323 of the second insulation porcelain 32 when the lead 16 is coupled to the connector 2, thus avoiding an undesirable drop of the connector 2 into the through hole 322, which allows the connector 2 to be pressed and laser-welded to secure the lead 16 in a constant position.

Figure 5A:
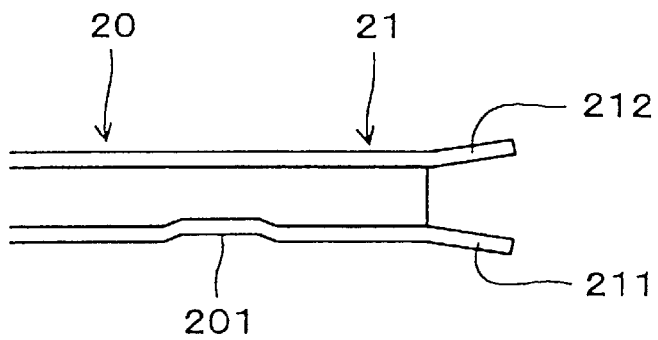
FIGS. 5(a) and 5(b) are longitudinal sectional views which show modifications of the connector of FIG. 3(a)

Both the extension 211 and the stopper 212 of each of the connectors 2 may alternatively be, as shown in FIG. 5(a), expanded outward. This facilitates ease of insertion of the lead 16 into the connector 2.

Figure 5B:
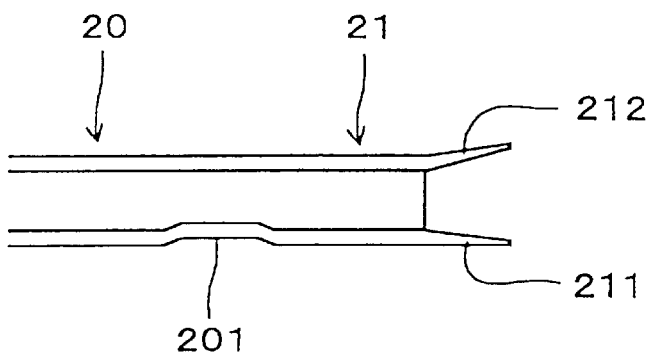

The extension 211 and the stopper 212 may also be, as shown in FIG. 5(b), chamfered or tapered. This provides for smooth insertion of the lead 16 into the connector 2.

Figure 6:
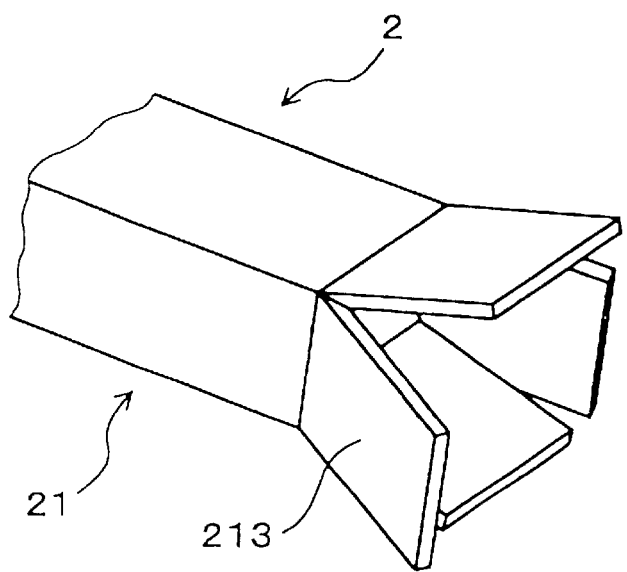
FIG. 6 is a partially perspective view which shows a modification of the connector of FIG. 3(a)

The head portion 21 may also, as shown in FIG. 6, have four extensions 213 expanding outward to work as stoppers. This absorbs shifts in location of the lead 16 from the end of the connector 2 in all directions and also facilitates ease of insertion of the lead 16 into the connector 2.

The connectors 2 may be formed to various shapes in cross section, as shown in FIGS. 7(a) to 7(f).

Figure 7A:
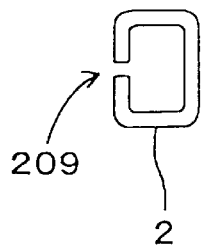
FIGS. 7(a), 7(b), 7(c), 7(d), 7(e), and 7(f) are sectional views taken along the line A—A in FIG. 2 which show variations in sectional shape of a connector.
Figure 7B:
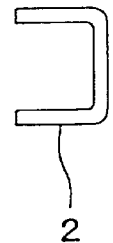
Figure 7C:
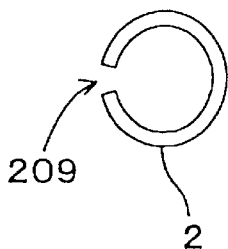
Figure 7D:
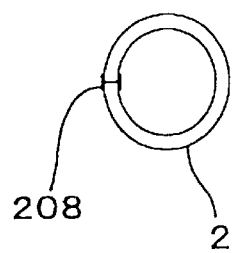
Figure 7E:
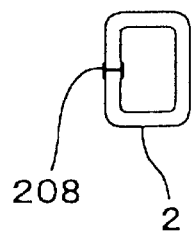
Figure 7F:
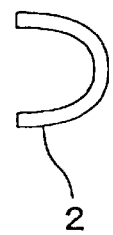

Specifically, the connector 2 of FIG. 7(a) has a longitudinally extending slit 209 formed in a side wall thereof. The connector of FIG. 7(b) is of C-shape in cross section defined by three side walls. The connector of FIG. 7(c) is of circular shape in cross section and has a longitudinally extending slit 209. The connector of FIG. 7(d) is, like FIG. 7(c), of circular shape in cross section, but has abutting ends 208 welded to each other. The connector of FIG. 7(e) is of rectangular shape in cross section and has abutting ends 208 welded to each other. The connector 2 of FIG. 7(f) is of U-shape in cross section.

Figure 8:
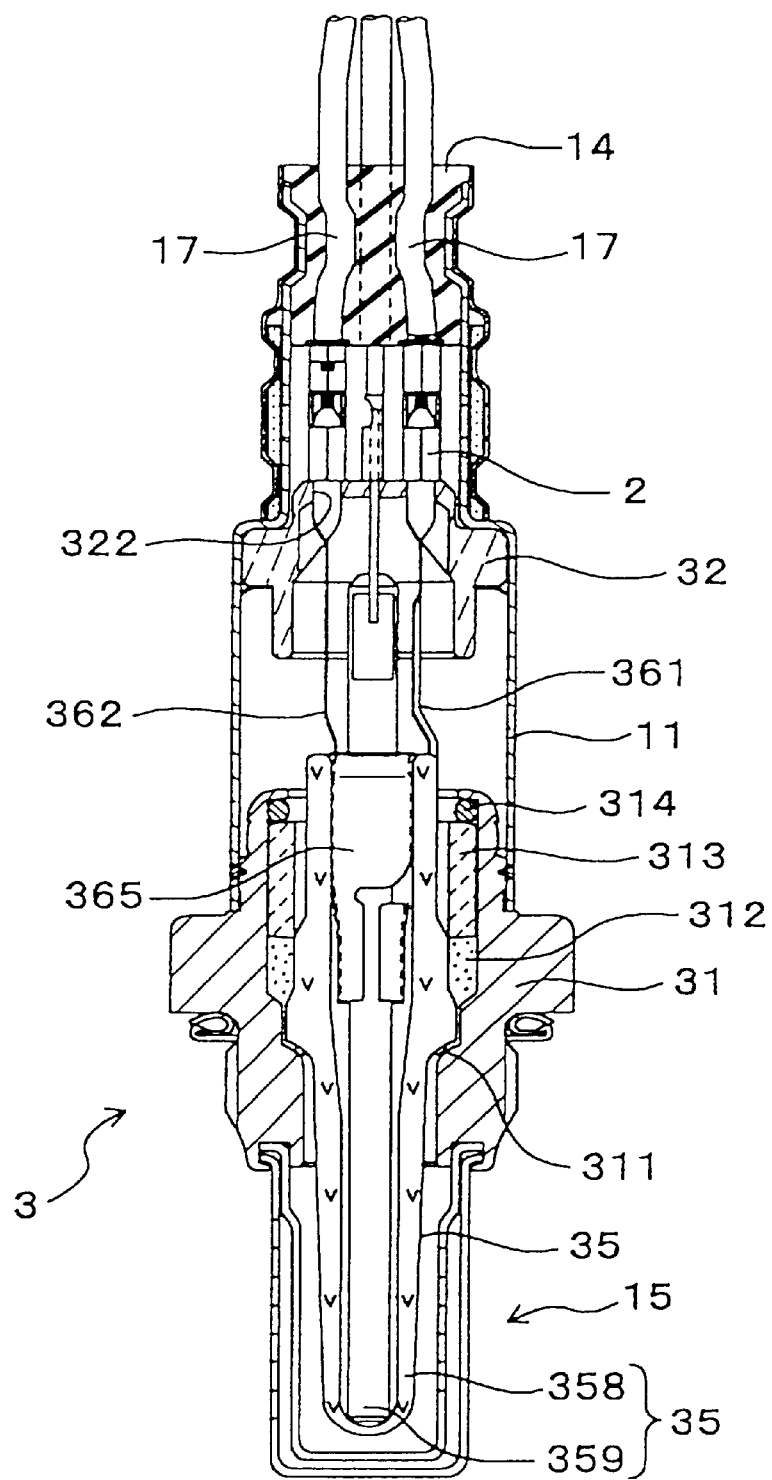
FIG. 8 is a longitudinal sectional view which shows a gas sensor according to the second embodiment of the invention.

FIG. 8 shows a gas sensor 3 according to the second embodiment of the invention which is equipped with a cup-shaped sensing element 35.

The sensing element 35 consists of a cup-shaped solid electrolyte body 358 and a bar-shaped heater 359. The solid electrolyte body 358 is retained in a hollow cylindrical housing 31. The heater 359 is disposed within the solid electrolyte body 358.

The sensing element 35 and the housing 31 are hermetically sealed by a packing ring 311 placed on an annular shoulder formed on an inner wall of the housing 30, a sealing powder 312, and a ceramic cylinder 313.

A metallic ring 314 is disposed on an end of the ceramic cylinder 313 and urged downward by a curved edge of the housing 31, as viewed in the drawing, to hold the sensing element 35 within the housing 31 firmly.

A lead 361 is provided for electric connection between one of the connectors 2 and the sensing element 35. The lead 361 is made of a conductive strip which has formed at an end thereof a ring fitted on the base end of the sensing element 35 leading to a gas measuring electrode (not shown) formed on an outer wall of the solid electrolyte body 358. A lead 362 made of a conductive strip is provided for electric connection between the heater 359 and one of the connectors 2. The lead 362 has formed at an end thereof a cylindrical heater holder 365 which is fitted on the end of the heater 359 to hold it within the solid electrolyte body 358 and placed in electric contact with a reference gas electrode (not shown) formed on an inner wall of the solid electrolyte body 358. The gas measuring electrode and the reference gas electrode are known, for example, in European Patent Application EP 0918215 A2 assigned to the same assignee as that of this application, disclosure of which is incorporated herein by reference.

The leads 361 and 362 extend through the holes 322 formed in an end surface of a hollow cylindrical insulation porcelain 32 and connect with the leads 17 through the connectors 2, respectively. The heater 359 is, like the solid electrolyte body 358, connected to the leads 17 through the connectors 2.

Other arrangements are identical with those in the first embodiment, and explanation thereof in detail will be omitted here.

Figure 9:
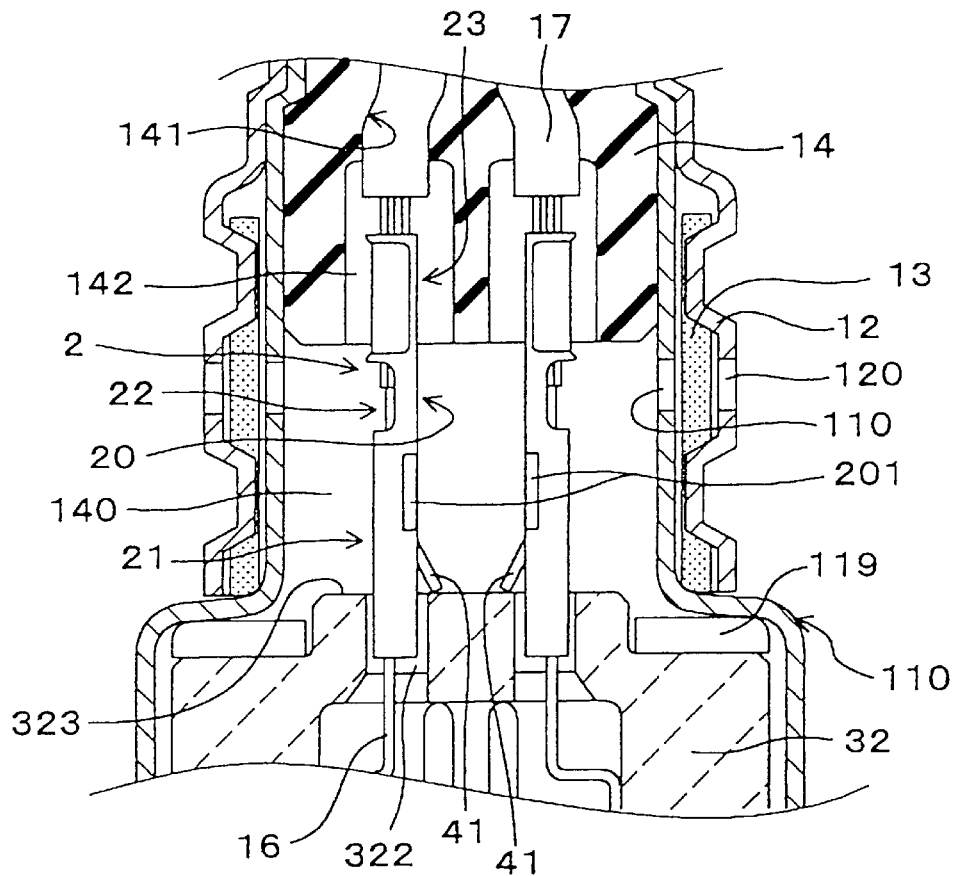
FIG. 9 is a partially sectional view which shows electric connections between a sensing element and leads extending outside a gas sensor according to the third embodiment of the invention.

FIG. 9 show a gas sensor according to the third embodiment of the invention which is different from the first embodiment only in that each of the connectors 2 has a stopper 41 formed on a side wall thereof. Other arrangements are identical, and explanation thereof in detail will be omitted here.

Figure 10:
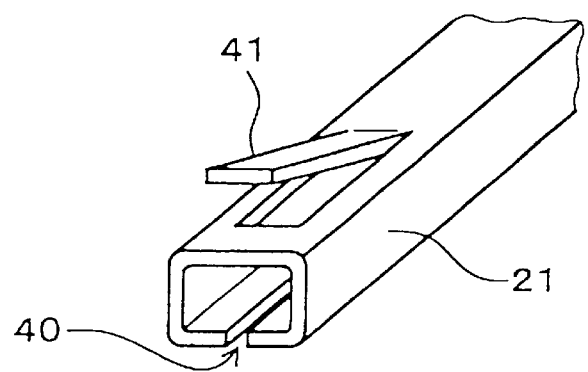
FIG. 10 is a partially perspective view which shows a connector of the third embodiment.

Each of the connectors 2 is, as clearly shown in FIG. 10, made of a hollow rectangular conductive member which has a longitudinally extending slit 40 formed on one side wall thereof and a strip sheared out from an opposite side wall to define the stopper 41. Each of the connectors 2 is, as shown in FIG. 9, inserted partially into one of the holes 322 in contact of the stopper 41 with the end wall 323 of the second insulation porcelain 32, thereby avoiding an undesirable drop of the connector 2 into the hole 323.

Figure 11:
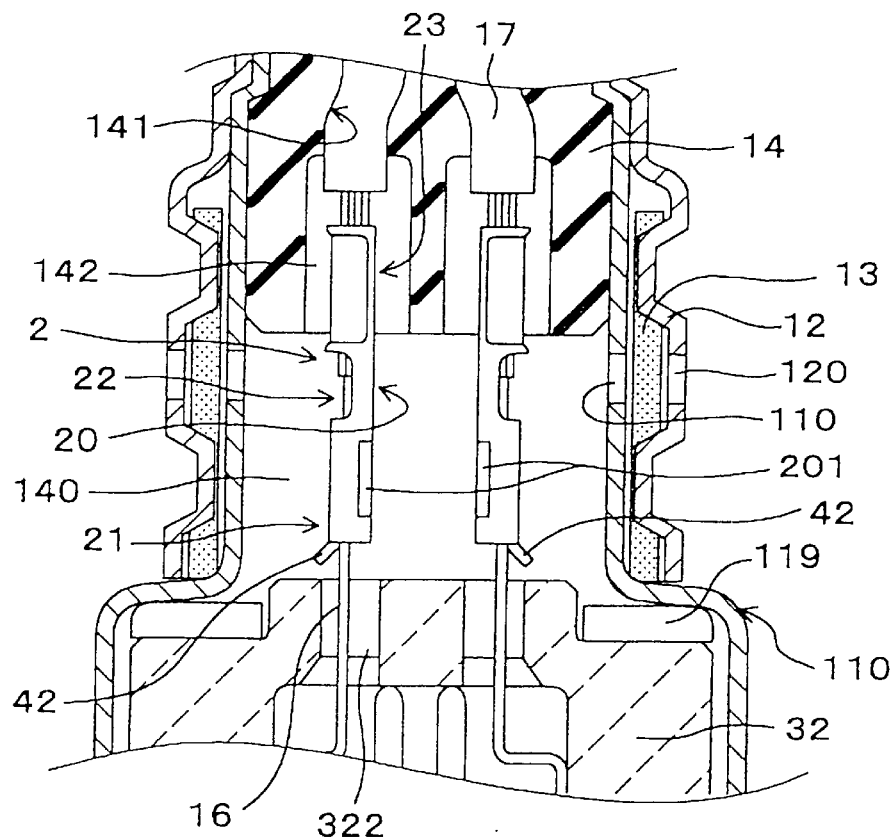
FIG. 11 is a partially sectional view which shows a gas sensor according to the fourth embodiment of the invention.

FIG. 11 shows a gas sensor according to the fourth embodiment of the invention which is different from the first embodiment only in structure of the leads 16. Other arrangements are identical, and explanation thereof in detail will be omitted here.

Figures 12A, 12B, 12C:
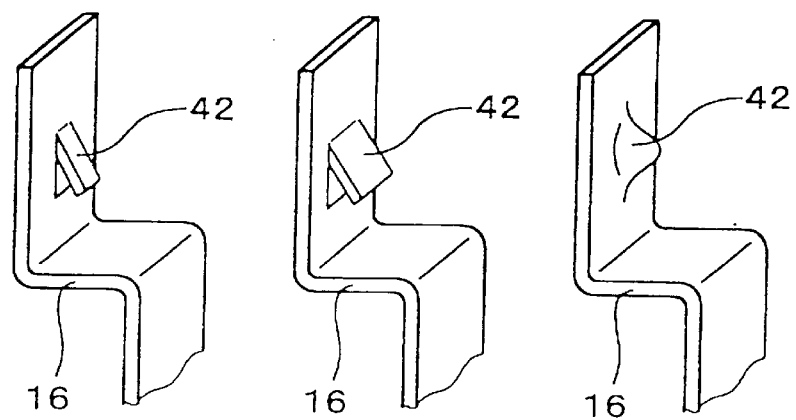
FIG. 12(a) is a perspective view which shows a lead with a stopper in the fourth embodiment.
FIGS. 12(b) and 12(c) are perspective views which show modifications of the lead of FIG. 12(a)

Each of the leads 16 is, as clearly shown in FIG. 12(a), made of a conductive plate which has a stopper 42 formed by shearing out a strip from a base portion of the conductive plate to be joined to the connector 2. The joining of the head 16 to the connector 2 is accomplished by inserting the base portion of the lead 16 into an end of the connector 2 as long as the stopper 42 advances and pressing the connector 2 in the same manner as described in the first embodiment. When the lead 16 is joined to the connector 2, the stopper 42 extends out of the hole 322 of the second insulation porcelain 32, thereby avoiding an undesirable drop of the connector 2 into the hole 322.

The stopper 42 may alternatively be, as shown in FIG. 12(b), made by shearing out half a width of the base portion of the lead 16 or pressing, as shown in FIG. 12(c), the base portion of the lead 16 to form a protrusion.

Figure 13:
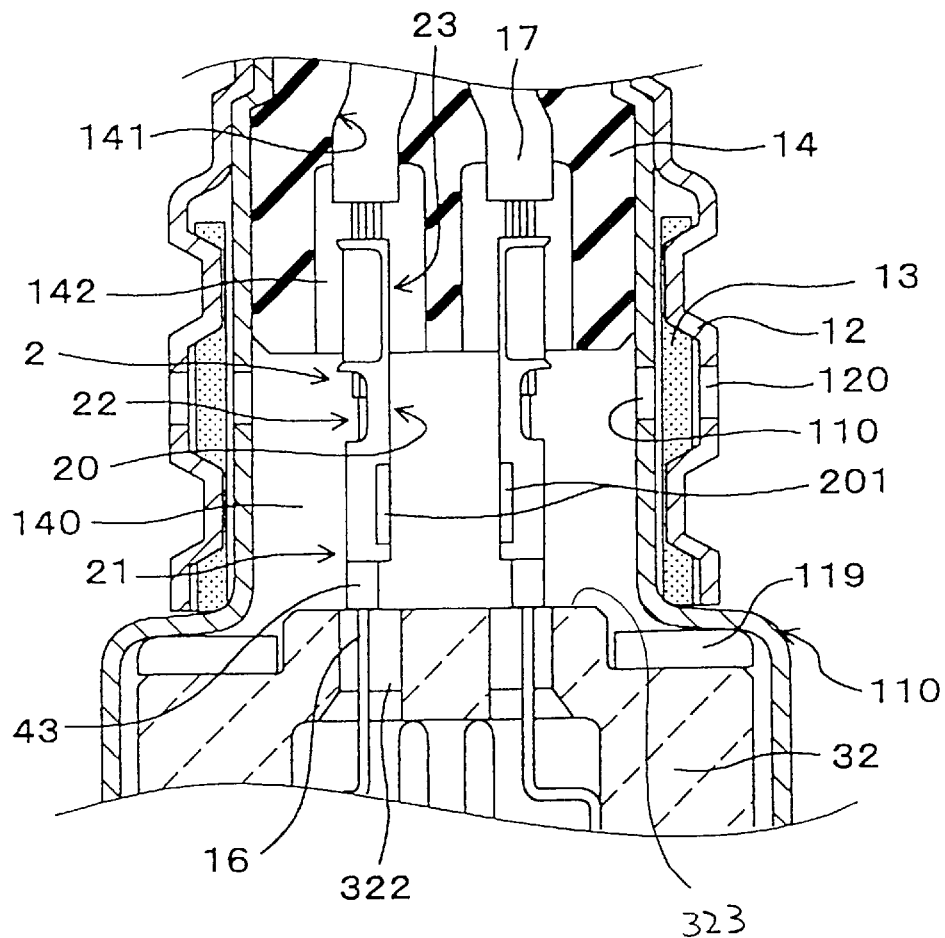
FIG. 13 is a partially sectional view which shows a gas sensor according to the fifth embodiment of the invention.

FIG. 13 shows a gas sensor according to the fifth embodiment of the invention which is different from the first embodiment only in that a stopper 43 is provided independently from each of the connectors 2. Other arrangements are identical, and explanation thereof in detail will be omitted here.

Figures 14A, 14B:
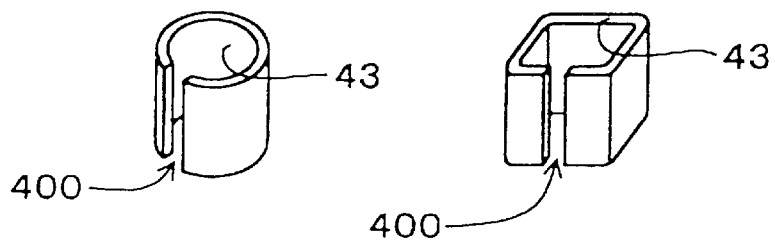
FIG. 14(a) is a perspective view which shows a stopper in the fifth embodiment.
FIG. 14(b) is a perspective view which shows a modification of the stopper in the fifth embodiment.

The stopper 43 is made of a material different from that of the lead 16 and formed by a hollow cylinder, as shown in FIG. 14(a), which has a slit 400 formed therein. The stopper 43 is disposed beneath each of the connectors 2 in partial contact with the end wall 323 of the second insulation porcelain 32, thereby avoiding an undesirable drop of the connector 2 into the hole 322 when the lead 16 is coupled to the connector 2. The stopper 43 may alternatively, as shown in FIG. 14(b), be made of a hollow member having a rectangular shape in cross section.

Figure 15:
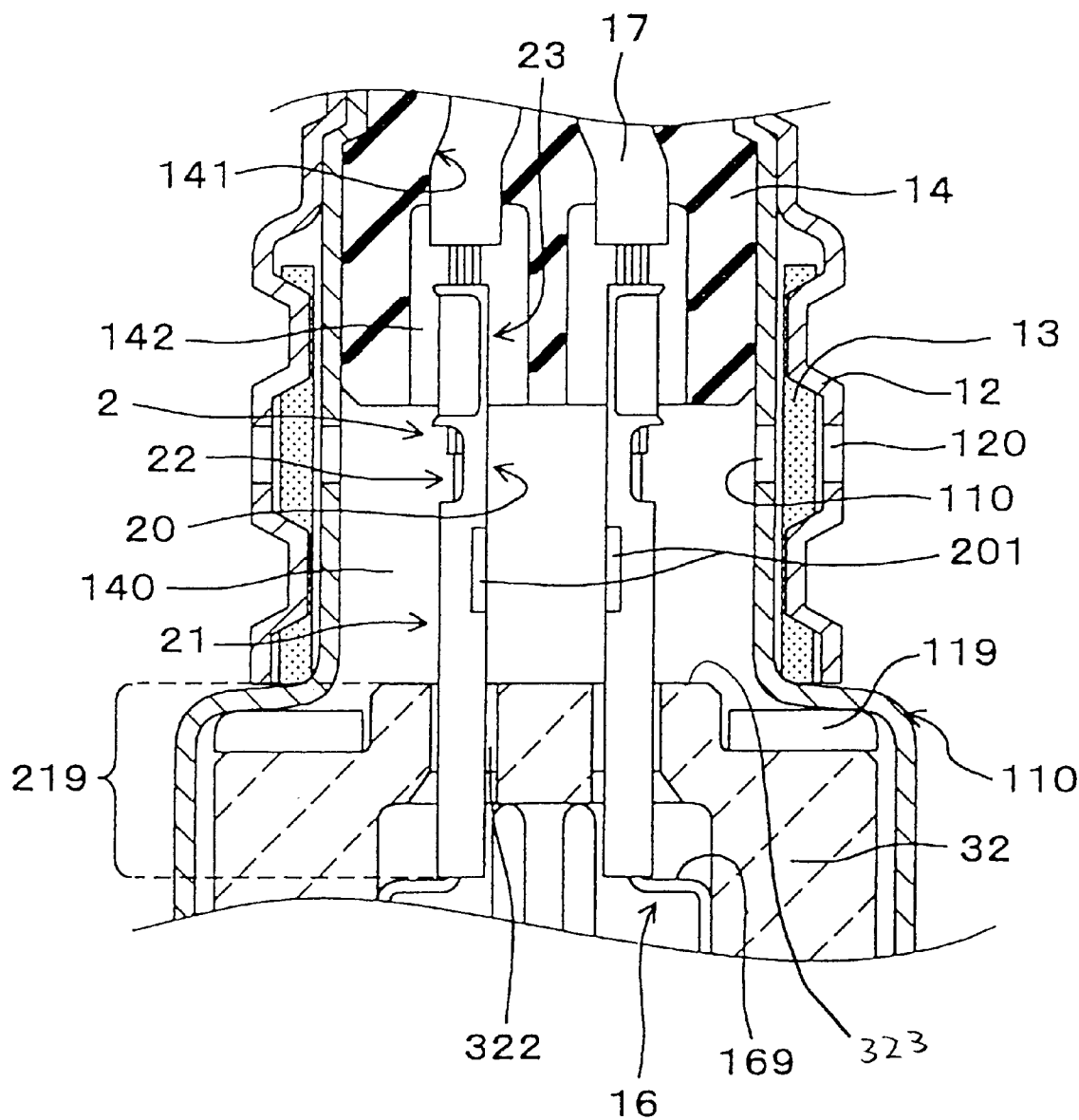
FIG. 15 is a partially sectional view which shows a gas sensor according to the sixth embodiment of the invention.
Figure 16A:
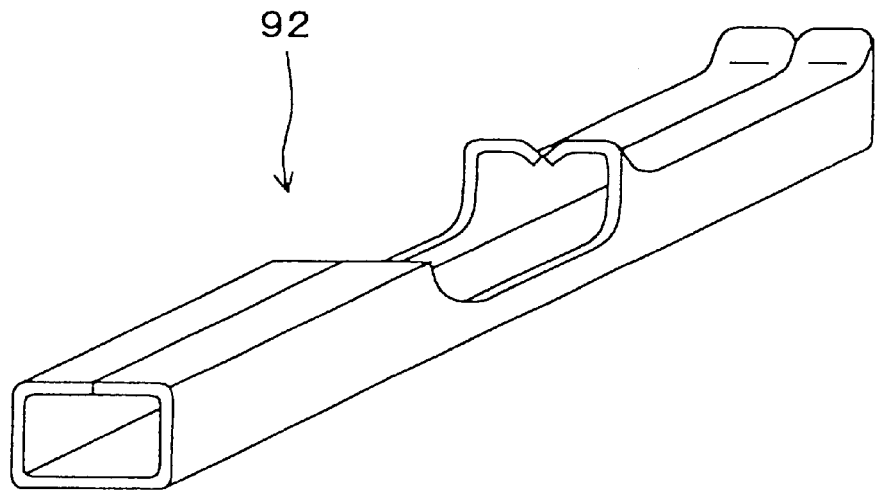
FIG. 16(a) is a perspective view which shows the structure of a connector mounted in a gas sensor which may be proposed to alleviate problems of the prior art.
Figure 16B:
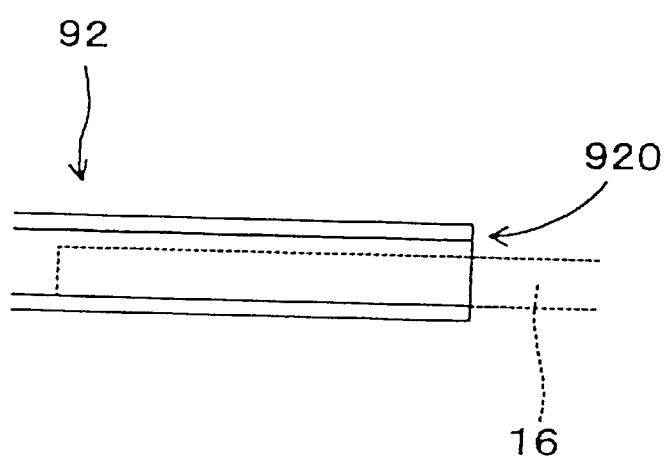
FIG. 16(b) is a longitudinal sectional view which shows the connector of FIG. 16(a)
Figure 17:
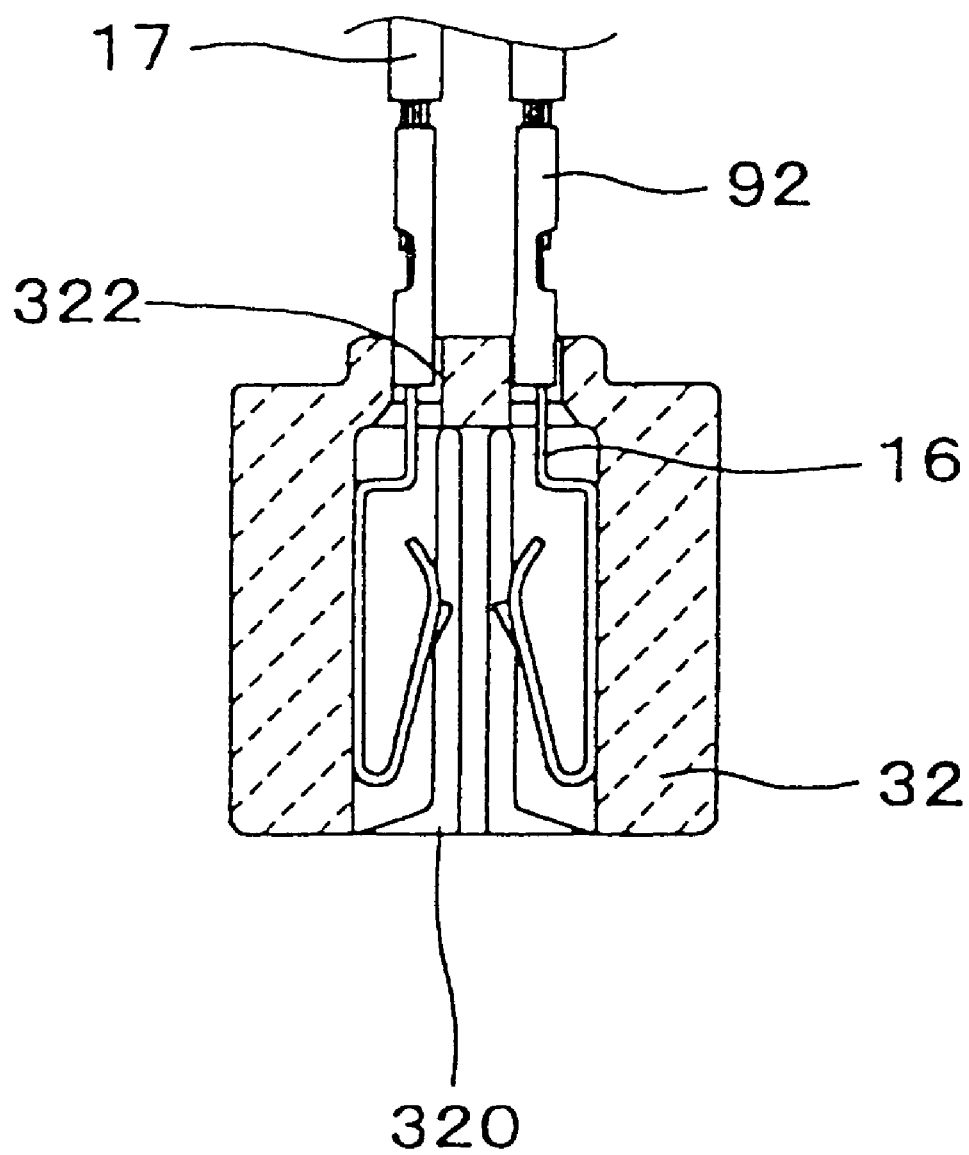
FIG. 17 is a partially longitudinal sectional view which shows a gas sensor in which the connector of FIG. 16(a) is installed.

FIG. 15 shows a gas sensor according to the sixth embodiment of the invention.

Each of the connector 2 has a hollow cylindrical extension 219 which passes through the hole 322 and engages a shoulder 169 of the lead 16. Specifically, the extension 291 is placed in contact with the shoulder 169 of the lead 16, thereby keeping the press portion 201 at a constant level from the end wall 323 of the second insulation porcelain 32. This allows the connector 2 to be pressed and laser-welded to secure the lead 16 in a constant position.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor comprising:
   a hollow cylindrical housing;
   a sensing element having a length which includes a sensing portion and a base portion, said sensing element being retained in said housing with the base portion projecting from said housing;
   a hollow insulating member provided so as to surround the base portion of said sensing element, said insulating member having a wall in which a set of through holes are formed;
   a cover covering said insulating member;
   first leads each having a first end portion and a second end portion, each of the first end portions being in electric contact with said sensing element within said insulating member, each of the second end portions passing through one of the through holes and projecting outside said insulating member;
   second leads each having a first end portion and a second end portion, the first end portion extending outside of the gas sensor for electric connection with an external device; and
   connectors establishing electric connections between said first leads and said second leads, respectively, each of said connectors having a lead-joint portion and a stopper, each of the lead-joint portions electrically joining the second end portion of one of said first leads and the second end portion of a corresponding one of said second leads, each of the stoppers being placed in contact with the wall of said insulating member.

2. A gas sensor as set forth in claim 1, wherein each of the stoppers is provided by an extension formed on an end of one of said connectors.

3. A gas sensor as set forth in claim 1, wherein each of the stoppers is provided by a portion of one of the connectors which extends outward.

4. A gas sensor as set forth in claim 1, wherein each of the stoppers has a tapered end wall for ease of insertion of the second end portion of one of said first leads.

5. A gas sensor as set forth in claim 1, each of the stoppers has walls which define a rectangular shape in cross section and have ends expanding outward so that the ends are placed outside one of the holes of said insulating member in contact with the wall of said insulating member.

6. A gas sensor as set forth in claim 1, wherein each of said connectors has a longitudinal slit formed therein.

7. A gas sensor as set forth in claim 1, wherein said first leads and said second leads are joined to said connectors by pressing the lead joint portions of said connector to plastically deform them or welding or soldering the lead-joint portions of said connectors and said first and second leads together.

8. A gas sensor comprising:
   a hollow cylindrical housing;
   a sensing element having a length which includes a sensing portion and a base portion, said sensing element being retained in said housing with the base portion projecting from said housing;
   a hollow insulating member provided so as to surround the base portion of said sensing element, said insulating member having a wall in which a set of through holes are formed;
   a cover covering said insulating member;
   first leads each having a first end portion and a second end portion, each of the first end portions being in electric contact with said sensing element within said insulating member, each of the second end portions passing through one of the through holes and projecting outside said insulating member;
   second leads each having a first end portion and a second end portion, the first end portion extending outside of the gas sensor for electric connection with an external device;
   connectors establishing electric connections between the second end portions of said first leads and the second end portions of said second leads, respectively; and
   stoppers provided on one of the second end portions of said first leads in contact with the wall of said insulating member.

9. A gas sensor as set forth in claim 8, wherein each of said connectors has a longitudinal slit formed therein.

10. A gas sensor as set forth in claim 8, wherein said first leads and said second leads are joined to said connectors by pressing the lead-joint portions of said connector to plastically deform them or welding or soldering the lead-joint portions of said connectors and said first and second leads together.

11. A gas sensor comprising:
    a hollow cylindrical housing;
    a sensing element having a length which includes a sensing portion and a base portion, said sensing element being retained in said housing with the base portion projecting from said housing;
    a hollow insulating member provided so as to surround the base portion of said sensing element, said insulating member having a wall in which a set of through holes are formed;

a cover covering said insulating member;

first leads each having a first end portion and a second end portion, each of the first end portions being in electric contact with said sensing element within said insulating member, each of the second end portions passing through one of the through holes and projecting outside said insulating member;

second leads each having a first end portion and a second end portion, the first end portion extending outside of the gas sensor for electric connection with an external device;

connectors establishing electric connections between the second end portions of said first leads and the second end portions of said second leads, respectively; and stoppers provided in contact with the wall of said insulating member to hold said connectors above the holes of said insulating member.

12. A gas sensor as set forth in claim 11, wherein each of said connectors has a longitudinal slit formed therein.

13. A gas sensor as set forth in claim 11, wherein said first leads and said second leads are joined to said connectors by pressing the lead-joint portions of said connector to plastically deform them or welding or soldering the lead-joint portions of said connectors and said first and second leads together.

14. A gas sensor comprising:

a hollow cylindrical housing;

a sensing element having a length which includes a sensing portion and a base portion, said sensing element being retained in said housing with the base portion projecting from said housing;

a hollow insulating member provided so as to surround the base portion of said sensing element, said insulating member having a wall in which a set of through holes are formed;

a cover covering said insulating member;

first leads each having a first end portion and a second end portion, each of the first end portions having a shoulder and being in electric contact with said sensing element within said insulating member, each of the second end portions passing through one of the through holes and projecting outside said insulating member;

second leads each having a first end portion and a second end portion, the first end portion extending outside of the gas sensor for electric connection with an external device;

connectors establishing electric connections between the second end portions of said first leads and the second end portions of said second leads, respectively; and stoppers each provided by an extension formed on an end of one of said connectors, placed in contact with the shoulder of the first end portion of one of said first leads to hold the one of said connector.

15. A gas sensor as set forth in claim 14, wherein each of said connectors has a longitudinal slit formed therein.

16. A gas sensor as set forth in claim 14, wherein said first leads and said second leads are joined to said connectors by pressing the lead-joint portions of said connector to plastically deform them or welding or soldering the lead-joint portions of said connectors and said first and second leads together.

* * * * *